US005705705A

United States Patent [19]

Brown et al.

[11] Patent Number: 5,705,705
[45] Date of Patent: Jan. 6, 1998

[54] OXIDATION OF ALKYLAROMATIC COMPOUNDS

[75] Inventors: Scott William Brown, Standish; Kevin Auty, Ossett, both of United Kingdom

[73] Assignee: Solvay Interox Limited, Warrington, England

[21] Appl. No.: 619,507

[22] PCT Filed: Sep. 26, 1994

[86] PCT No.: PCT/GB94/02080

§ 371 Date: Mar. 26, 1996

§ 102(e) Date: Mar. 26, 1996

[87] PCT Pub. No.: WO95/09139

PCT Pub. Date: Apr. 6, 1995

[30] Foreign Application Priority Data

Sep. 28, 1993 [GB] United Kingdom ............... 9319945

[51] Int. Cl.⁶ .................................................. C07C 45/27
[52] U.S. Cl. ...................................... 568/430; 568/420
[58] Field of Search ......................................... 568/430

[56] References Cited

FOREIGN PATENT DOCUMENTS

WO 93/00319  1/1993  United Kingdom ............ C07C 45/28

OTHER PUBLICATIONS

Ma, Jianwei et al; "Controlled oxidation of toluene to oxygen–containing compounds"; (J. Shiyou Huagong; 21(4), 228–31 (1992).

Yazu Kazumasa et al; Chemical Abstracts;vol. 112;219165x (J. Chem. Soc., Japan, (1), 92–96 (1990).

*Primary Examiner*—C. Warren Ivy
*Assistant Examiner*—Sreeni Padmanabhan
*Attorney, Agent, or Firm*—Larson & Taylor

[57] ABSTRACT

A process for the oxidation of alkylaromatic compounds is provided. The process comprises oxidizing a substrate alkylaromatic compound with a peroxygen compound in the presence of a source of cerium (III) or (IV), a source of bromide and a carboxylic acid or anhydride solvent. Preferably, the source of cerium is cerium (III) acetate, the source of bromide is sodium bromide and the solvent is acetic or propionic acid. The process is particularly suited to the selective oxidation of methylaromatic compounds to the corresponding aldehydes.

24 Claims, No Drawings

OXIDATION OF ALKYLAROMATIC COMPOUNDS

This is the US National Stage Application of PCT/GB94/02080 filed Sep. 26, 1994 now WO95/09139 published Apr. 6, 1995.

This invention concerns a process for the oxidation of alkylaromatic compounds. More specifically, this invention concerns a catalysed process for the oxidation of alkylaromatic compounds with peroxygen compounds.

The oxidation of alkylaromatic compounds is a desirable reaction in organic chemistry because it permits the conversion of a readily available organic substrate having only limited reactivity into a compound including more reactive functional groups and hence having greater reactivity. Oxidation of alkylaromatic compounds commonly involves the oxidation of an alkyl hydrogen which requires the use of a relatively strong oxidant. It is therefore readily apparent that such an oxidant can often readily be employed for the oxidation of other more easily oxidised functional groups such as alcohols.

Many systems have been proposed for carrying out the oxidation of alkylaromatic compounds, including the use of transition metal oxides such as manganese dioxide, potassium permanganate and chromium oxide, and other oxidants such as organic peracids and air or gaseous oxygen. One particularly desirable oxidant that has been employed comprises an aqueous solution of hydrogen peroxide. In order to successfully employ hydrogen peroxide in the oxidation of alkylaromatic compounds it is often necessary to employ some other component such as a catalyst, for example, cobalt species, or a co-reagent, such as hydrogen bromide. However, it remains desirable to identify alternative and further oxidation systems for the oxidation of alkylaromatic compounds.

The oxidation of an alkylaromatic can be regarded as proceeding via a number of stages i.e. alkyl→alcohol→carbonyl compound→carboxyl compound (if appropriate). In addition, the presence of additional reagents may lead to the formation of other compounds, for example mono- and/or di-brominated species in the case of a bromide co-reagent. These compounds can sometimes be easily oxidised and/or hydrolysed to produce alcohols, carbonyl or carboxyl compounds. It will be recognised that once an alcohol or carbonyl compound, especially an aldehyde has been formed, the oxidising conditions can often result in this compound being further oxidised. For this reason, it is often difficult to halt the oxidation at one of the intermediate oxidation products, and on account of this, such intermediate compounds can command a premium price. It would therefore be desirable to identify an oxidation system for alkylaromatic compounds that was effective at producing such intermediate products and/or which produced compounds that could be conveniently converted to such intermediate compounds.

It is an object of the present invention to provide an alternative and further system for the oxidation of alkylaromatic compounds.

It is a further objective of at least some embodiments of the present invention to provide a process for the oxidation of alkylaromatic compounds that is effective at producing intermediate oxidation products and/or which produces compounds that can be conveniently converted to such intermediate compounds.

According to the present invention, there is provided a catalysed process for the oxidation of alkylaromatic compounds with a peroxygen compound in a reaction medium, characterised in that the catalyst comprises a source of cerium (III) or (IV), the reaction medium comprises a source of bromide ions and a solvent selected from the group consisting of carboxylic acids and anhydrides, and the alkylaromatic compound comprises an alkyl hydrogen atom, and optionally a hydroxyl group, bonded to the carbon alpha to the aromatic ring.

According to a second aspect of the present invention, there is provided a process for the selective oxidation of methylaromatic compounds to aldehydes with a peroxygen compound in a reaction medium, characterised in that the catalyst comprises a source of cerium (III) or (IV), and the reaction medium comprises a source of bromide ions and a solvent selected from the group consisting of carboxylic acids and anhydrides.

Sources of cerium that can be employed in The catalyst system and the process according to the present invention include cerium salts and cerium complexes. The sources of cerium are usually introduced into the reaction medium in oxidation states (III) or (IV). However, it will be recognised that a cerium source in a lower oxidation state can be introduced into the reaction medium, with oxidation in situ occurring to produce a cerium species in oxidation state (III) or (IV). In many instances, however, the cerium source is cerium (III). Examples of suitable cerium salts that can be employed include oxides, hydroxides, halides, carbonates, sulphates, acetates and nitrates. The most preferred cerium source is cerium (III) acetate.

In the process according to the present invention, the source of cerium is usually present in a mole ratio of substrate to cerium of less than about 5000:1, preferably from about 3000:1 to about 10:1, and particularly preferably from about 2500:1 to about 1500:1. Although it will be recognized that the cerium source can be present in an amount greater than this, it is believed that the use of such a greater amount is not necessary, and therefore represents unnecessary expense.

The source of bromide ions that is employed in the process according to the present invention can be selected from the group consisting of elemental bromine, hydrogen bromide and bromide salts. Suitable bromide salts include alkali metal bromides, particularly sodium and potassium bromide, alkaline earth metal bromides such as magnesium and calcium bromide and amine-derived salts such as quaternary ammonium bromides and ammonium bromide. In some embodiments of the present invention, the source of bromide ions comprises cerium bromide, and this can therefore serve, at least partly, as both cerium and bromide ion source.

The mole ratio of cerium source to bromide source is usually selected in the range from about 10:1 to about 1:3000, preferably from about 1:100 to about 1:1500. In certain embodiments of the present invention, good results have been achieved employing a mole ratio of cerium source to bromine source in the range of from about 1:500 to 1:1000.

The solvent in the process according to the present invention comprises a carboxylic acid or carboxylic anhydride. Usually, the acid or anhydride will contain from 1 to about 6 carbon atoms, and suitable examples include acetic anhydride, acetic acid and propionic acid. The most preferred solvent is acetic acid. The weight ratio of solvent to substrate can be selected from a very wide range depending, for example, on the solubility of the substrate, but will often be in the range from about 100:1 to about 1:5.

It will be recognised that it is possible to employ additional solvents. Such additional solvents can be present at a wide weight ratio to the carboxylic acid or anhydride solvent, depending for example on the solubility of the substrate. The weight ratio of carboxylic acid or anhydride to additional solvent is often selected in the range of from about 1:10 to about 10:1, often from 1:2 to about 8:1, usually from about 2:1 to about 6:1. The additional solvents are usually selected to be resistant to oxidation, and examples include chlorinated solvents such as dichloromethane, 1,2-dichloroethane, chloroform and carbon tetrachloride, oxidation resistant alcohols such as t-butanol, esters such as ethyl acetate and isopropyl acetate, nitriles such as acetonitrile, amides such as dimethyl formamide, and ethers such as 1,4-dioxane and tetrahydrofuran.

The reaction medium can comprise water prior to the addition of peroxygen compound, particularly when a carboxylic acid is employed as solvent. When this is the case, the amount of water is often from 5% to 35%, preferably from 15% to 25% by weight, based on the weight of carboxylic acid employed. In some embodiments of the present invention, the presence of water in the reaction medium prior to the addition of peroxygen compound has been found to improve the selectivity of the process to aldehyde, and reduce the selectivity to monobrominated product.

Peroxygen compounds that can be employed in the process according to the present invention comprise hydrogen peroxide, urea peroxide, persalts including sodium percarbonate and sodium perborate, and peracids, for example Caro's acid or peracetic acid. Preferably, the peroxygen compound is an aqueous solution of hydrogen peroxide.

The alkylaromatic compounds which can be oxidised by the process of the present invention are those which comprise at least one alkyl, preferably a ($C_1$–$C_6$) alkyl, substituent having at least one hydrogen atom or hydroxy group at the alpha position relative to the aromatic ring. Although higher alkyl substituents may be oxidised by the process of the present invention, such as those having up to 30 carbon atoms, ($C_1$–$C_6$) alkyl substituents are preferred. From the preferred group of substituents, straight chain ($C_1$–$C_6$) alkyl substituents and branched chain alkyl substituents having less than 5 carbons are most preferred. Examples of alkylaromatic compounds which can be oxidised by the present invention include alkylbenzenes, such as toluene, ethylbenzene, p-t-butyltoluene, cumene, o-, m- or p-xylenes, o-, m- or p-diethylbenzenes and polynuclear alkylaromatic compounds such as the mono-, di- and tri-alkyl naphthalenes, e.g. methyl naphthalenes, ethyl naphthalenes and dimethylnaphthalenes.

The alkyl substituent or substituents of the alkylaromatic compounds can be any substituted alkyl which may be oxidised to an alcohol, a ketone or carboxylic acid as may be appropriate. Such substituted alkyls commonly have at least one hydrogen atom, and optionally a hydroxy group, at the alpha position relative to the aromatic ring. Alkyls substituted with at least one phenyl-, hydroxy-, halo- or oxy- substituent are examples of the substituted-alkylaromatic compounds which may be oxidised by the process of the present invention. For example, when the alkyl- substituent is methyl-, the methyl- may be a mono- or di-substituted methyl- of the formula —$CHR^1R^2$ where $R^1$ and $R^2$ are independently selected from the group consisting of H-, substituted or unsubstituted phenyl-, —OH and —hal (—hal is —F, —Cl, —Br or —I). Examples of substituted-alkylaromatic compounds are diphenylmethane and diphenylethane. Preferably, the alkyl group is a methyl group.

The alkylaromatic compounds that can be oxidised by the process according to the present invention can comprise an aromatic ring which is substituted with one or more substituents. The range of substituents that can be present will depend on the presence or absence of a hydroxy group at the position alpha to the aromatic ring, and on the position of substitution, i.e. ortho, meta or para to the alkyl group. When a hydroxy group is present alpha to the aromatic ring, the substituent can be one or more of nitro, alkyl, halo, aldehyde, ketone, carboxylate or sulphonic acid groups, and preferably alkyl, and the substituent can be present at any position on the ring.

When a hydroxy group alpha to the aromatic ring is not present, the nature of the substituent will depend on the position of substitution. Substituents meta to the alkyl group can be selected from the above list for when the hydroxy group is present. Substituents ortho and/or para to the alkyl group must not be such that the aromatic ring is net strongly deactivated, such as by the presence by themselves of strongly electron withdrawing groups such as nitro or aldehyde groups, although it is believed that the effect of such groups may be ameliorated by the presence of one or more activating, electron donating groups such as alkoxy or amino groups. The aromatic ring must not be net strongly activated to ring bromination, such as by the presence by themselves of alkoxy and amino groups, although it is believed that the effect of such groups can be ameliorated by the presence of one or more deactivating, electron withdrawing groups such as nitro, aldehyde or carboxyl groups. In many embodiments, substituents ortho and/or para to the alkyl group when a hydroxy is not present alpha to the aromatic ring are selected from activating or neutral groups such as alkyl and halo groups.

The peroxygen compound can be introduced into the reaction medium in stoichiometric, sub-stoichiometric or greater than stoichiometric amounts, based on the mole ratio of peroxygen compound to alkylaromatic. It may be preferable to employ a sub-stoichiometric amount of peroxygen compound when the substrate is particularly sensitive to further oxidation. In most embodiments, however, it is preferred to employ at least a stoichiometric amount of peroxygen compound, and often peroxygen compound an excess of the stoichiometric amount, such as up to 10 moles of peroxygen compound per mole of alkylaromatic, i.e. up to an excess of 9 times, and preferably from about 1.5 to about 5 moles of peroxygen compound per mole of alkylaromatic, i.e. an excess of about 0.5 to about 4 times above the stoichiometric amount.

When the peroxygen compound is hydrogen peroxide, it is preferably introduced into the reaction medium in the form of a concentrated aqueous solution, often comprising from about 25 to about 70% w/w, and frequently from about 30 to 50% w/w hydrogen peroxide.

When the peroxygen compound is a peracid and particularly peracetic acid, it is conveniently introduced either as an equilibrium aqueous solution or as a distilled product comprising a solution of the peracid in the corresponding acid which is substantially free of water and hydrogen peroxide. The concentration of peracid is often in the range from about 10% to about 50% w/w, preferably 30% to about 45% w/w.

When the peroxygen compound comprises urea peroxide, sodium percarbonate or sodium perborate, it is conveniently introduced as a solid, an aqueous solution or as an aqueous slurry, Preferably, the peroxygen compound is introduced into the reaction medium which contains both the substrate and catalyst system, and particularly preferably it is introduced gradually, for example over a period of from 15 minutes to 4 hours. In certain embodiments of the present invention, a plurality of peroxygen compound additions, with optionally a plurality of additions of source of bromide ions, at intervals during the reaction can be employed.

The process according to the present invention is usually carried out at elevated temperature, typically from 50° C. up to the reflux temperature of the reaction medium, and particularly from about 60° to about 85° C. Particularly for substrates which boil under standard atmospheric pressure at lower temperatures than the desired reaction temperature, the reaction may be conducted at an elevated pressure selected so as to permit the desired temperature to be attained, but of course the higher boiling substrates may likewise be reacted at elevated pressure if desired.

In certain embodiments of the present invention, in addition to the oxidised alkylaromatic compounds, the process produces significant quantities of monobrominated alkylaromatic compounds. Although it is desirable to minimise the quantity of brominated products, their presence is not actually too detrimental to the viability of the process, especially when they can be converted into a carbonyl compound or alcohol. Such a conversion may be effected by acid or alkali catalysed hydrolysis, followed if desired by further oxidation.

The product(s) of the process according to the present invention can be separated from the reaction medium by conventional means well known to those skilled in the art depending on the physical form of the product at the temperature the separation is to occur. If the product is a solid, separation will often be achievable by filtration or centrifugation. If the product is a liquid, separation will often be achievable by distillation, solvent extraction or an alternative method such as column chromatography.

According to a preferred aspect of the present invention, there is provided a catalysed process for the oxidation of alkylaromatic compounds with a peroxygen compound in a reaction medium, characterised in that the catalyst comprises cerium triacetate, the reaction medium comprises sodium bromide and acetic acid, and the alkylaromatic compound comprises a methyl group.

Having described the invention in general terms, specific embodiments thereof are described in greater detail by way of example only. All yields quoted are based on the weight of substrate added.

COMPARISON 1

4-t-butyltoluene (4.4 g, 30 mmol), sodium bromide (0.76 g) and acetic acid (60 g) were charged to a reactor and heated to 70° C. with stirring. To this reaction medium was added 35% aqueous hydrogen peroxide solution (11.65 g, 120 mmol) over a period of 3 hours using a peristaltic pump. The reaction was continued for a period of 2 hours after completion of the hydrogen peroxide addition, and then the reaction medium analysed by gas chromatography and HPLC.

The results of the analysis showed that only 29% of the 4-t-butyltoluene was converted, yielding 5.4% 4-t-butylbenzaldehyde, 6.6% 4-t-butylbenzylbromide, 9.2% 4-t-butylbenzylacetate and 3.8% 4-t-butylbenzyl alcohol. This represents a selectivity to aldehyde of only 19%, and a total selectivity to desired products (aldehyde, alcohol and bromide) of 55%.

COMPARISON 2

4-t-butyltoluene (4 g, 27 mmol) and acetic acid (60 g) were charged to a reactor and heated to 70° C. with stirring. To this reaction medium was added 35% aqueous hydrogen peroxide solution (5.2 g, 53 mmol) over a period of 1.5 hours using a peristaltic pump. The reaction was continued for a period of 4.5 hours after completion of the hydrogen peroxide addition, and then the reaction medium analysed by gas chromatography and HPLC.

The results of the analysis showed that none of the 4-t-butyltoluene was converted, indicating that no reaction had taken place.

COMPARISON 3

4-t-butyltoluene (4 g, 27 mmol), sodium bromide (0.5 g), cerium triacetate (0.2 g) and t-butanol (60 g) were charged to a reactor and heated to 70° C. with stirring. To this reaction medium was added 35% aqueous hydrogen peroxide solution (11.65 g, 120 mmol) over a period of 3 hours using a peristaltic pump. The reaction was continued for a period of 3 hours after completion of the hydrogen peroxide addition, and then the reaction medium analysed by gas chromatography.

The results of the analysis showed that no substrate had been converted, indicating that no reaction had taken place.

EXAMPLE 4

The procedure of Comparison 1 was followed, with the addition of 0.015 g of cerium triacetate to the reaction medium prior to heating.

The results of the analysis showed that 60% of the 4-t-butyltoluene was converted, yielding 29% 4-t-butylbenzaldehyde, 7.2% 4-t-butylbenzylbromide, 14% 4-t-butylbenzylacetate, 7.1% 4-t-butylbenzyl alcohol and 2.3% 4-t-butyl benzoic acid. This represents a selectivity to aldehyde of 48%, and a total selectivity to desired products (aldehyde, alcohol and bromide) of 72%.

EXAMPLE 5

The procedure of Example 4 was followed, except that the acetic acid was replaced with a mixture of 48 g acetic acid and 12 g t-butanol.

The results of the analysis showed that 61% of the 4-t-butyltoluene was converted, yielding 30% 4-t-butylbenzaldehyde, 7% 4-t-butylbenzylbromide, 9% 4-t-butylbenzylacetate, 6% 4-t-butylbenzyl alcohol and 4% 4-t-butylbenzoic acid. This represents a selectivity to aldehyde of 50%, and a total selectivity to desired products (aldehyde, alcohol and bromide) of 71%.

EXAMPLE 6

The procedure of Example 4 was followed, except that the acetic acid was replaced with 60 g propionic acid.

The results of the analysis showed that 49% of the 4-t-butyltoluene was converted, yielding 24% 4-t-butylbenzaldehyde, 10% 4-t-butylbenzylbromide, 5.2% 4-t-butylbenzylpropionate, 6% 4-t-butylbenzyl alcohol and 5.1% 4-t-butylbenzoic acid. This represents a selectivity to aldehyde of 49%, and a total selectivity to desired products (aldehyde, alcohol and bromide) of 82%.

EXAMPLE 7 p-xylene (2.9 g 27 mmol), sodium bromide (0.5 g), cerium triacetate (0.2 g) and acetic acid (50 g) were charged to a reactor and heated to 70° C. To this reaction medium was added 35% aqueous hydrogen peroxide solution (6.3 g, 67 mmol) over a period of 1.5 hours using a peristaltic pump. The reaction was then continued for a period of 1 hour after completion of the hydrogen peroxide addition, when a further 0.5 g of sodium bromide was added, and a further 6.3 g of 35% aqueous hydrogen peroxide solution was added over 1.5 hours via a peristaltic pump. After the completion of the second hydrogen peroxide addition, the reaction medium was analysed by gas chromatography and HPLC. The results of the analysis showed that 80% of the xylene was converted, yielding 61% 4-methylbenzaldehyde and 6.6% 4-methylbenzylbromide. This represents a selectivity to aldehyde of 76%, and a selectivity to desired products of 84%.

EXAMPLE 8

4-chlorotoluene (3.4 g 27 mmol), sodium bromide (4.9 g), cerium triacetate (0.6 g) and acetic acid (50 g) were charged to a reactor and heated to 70° C. To this reaction medium was added 35% aqueous hydrogen peroxide solution (6.3 g, 67 mmol) over a period of 1.5 hours using a peristaltic pump. The reaction was then continued for a period of 1 hour after completion of the hydrogen peroxide addition and then the reaction medium was analysed by gas chromatography and HPLC.

The results of the analysis showed that 26% of the 4-chlorotoluene was converted, yielding 52% 4-chlorobenzaldehyde and 48% 4-chlorobenzylbromide. This represents a selectivity to aldehyde of 52%, and a selectivity to desired products of 100%.

EXAMPLE 9

4-t-butyltoluene (27 mmol), cerium acetate (0.6 mmol), sodium bromide (5 mmol) and acetic acid (50 g) were charged to a reactor and heated to 70° C. with stirring. To this reaction medium was added 35% aqueous hydrogen peroxide solution (54 mmol $H_2O_2$) over a period of 1 hour using a peristaltic pump. The reaction was continued for a period of 1 hour after completion of the hydrogen peroxide addition, and then the reaction medium sampled and analysed by gas chromatography and HPLC. A further 54 mmol $H_2O_2$ as 35% w/w aqueous solution was added to the reaction medium over 1 hour, the reaction continued for a further 1 hour, when the reaction medium was sampled and analysed. Again, a further 54 mmol $H_2O_2$ as 35% w/w aqueous solution was added to the reaction medium over 1 hour, the reaction continued for a further 1 hour, giving a total reaction time of 6 hours from the commencement of the first hydrogen peroxide addition, when the reaction medium was sampled and analysed. The results of the analysis are given below.

| Analysis time | 2 hours | 4 hours | 6 hours |
| --- | --- | --- | --- |
| Substrate conversion (%) | 30 | 50 | 55 |
| Aldehyde Yield (%) | 17.6 | 28 | 36.4 |
| Aldehyde Selectivity (%) | 58.7 | 56 | 66.2 |
| Monobromide yield (%) | 6.3 | 5 | 1.8 |
| Monobromide selectivity (%) | 21 | 10 | 3.3 |
| Alcohol yield (%) | 3.8 | 7 | 8.1 |
| Alcohol selectivity (%) | 12.7 | 14 | 14.7 |
| Acetate yield (%) | 2.0 | 9 | 8.3 |
| Acetate selectivity (%) | 6.7 | 18 | 15.1 |
| Total selectivity to desired products (%) | 92.4 | 80 | 83.7 |

EXAMPLE 10

The general method of Example 9 was followed, except that NaBr (2.5 mmol) was added to the reaction medium immediately prior to the commencement of the second and third hydrogen peroxide additions.

The results of the analysis are given below.

| Analysis time | 2 hours | 4 hours | 6 hours |
| --- | --- | --- | --- |
| Substrate conversion (%) | 30 | 57 | 70 |
| Aldehyde Yield (%) | 17.6 | 38 | 50 |
| Aldehyde Selectivity (%) | 58.7 | 67 | 71 |
| Monobromide yield (%) | 8.4 | 6 | 3 |
| Monobromide selectivity (%) | 28.0 | 10 | 4 |
| Alcohol yield (%) | 0.8 | 7 | 5 |
| Alcohol selectivity (%) | 2.7 | 12 | 7 |
| Acetate yield (%) | 2.2 | — | 8 |
| Acetate selectivity (%) | 7.3 | — | 11 |
| Total selectivity to desired products (%) | 89.4 | 89 | 82 |

EXAMPLES 11, 12 and 13

In Example 11, 4-t-butyltoluene (27 mmol), cerium acetate (0.6 mmol), sodium bromide (5 mmol) and acetic acid (50 g) were charged to a reactor and heated to 70° C. with stirring. To this reaction medium was added 35% aqueous hydrogen peroxide solution (54 mmol $H_2O_2$) over a period of 1 hour using a peristaltic pump. The reaction was continued for a period of 5 hours after completion of the hydrogen peroxide addition, and then the reaction medium sampled and analysed by gas chromatography and HPLC. In Example 12, the method of Example 11 was followed, except that 5 g water was added to the reaction medium prior to heating to 70° C. In Example 13, the method of Example 12 was followed, except that 10 g water was added. The results are given below.

| Example Number: | 11 | 12 | 13 |
| --- | --- | --- | --- |
| Substrate conversion (%) | 41.4 | 41.4 | 41.0 |
| Aldehyde Yield (%) | 20.5 | 26.1 | 28.0 |
| Aldehyde Selectivity (%) | 49.5 | 63.0 | 68.0 |
| Monobromide yield (%) | 13.9 | 2.6 | 0.0 |
| Monobromide selectivity (%) | 33.6 | 6.2 | 0.0 |
| Alcohol yield (%) | 3.8 | 9.1 | 10.5 |
| Alcohol selectivity (%) | 9.0 | 21.9 | 25.6 |
| Acetate yield (%) | 3.2 | 3.6 | 2.5 |
| Acetate selectivity (%) | 7.7 | 8.6 | 6.0 |
| Total selectivity to desired products (%) | 92.1 | 91.1 | 93.6 |

The results of Examples 4 to 13 above clearly show the benefit of the instant invention in providing a process for the oxidation of alkylaromatic compounds. The results obtained were significantly better than those achieved in comparisons 1 to 3 when at least one of cerium source, bromide source or carboxylic acid/anhydride solvent was omitted. The result of Example 8 showed that a deactivated substrate could be oxidised in good selectivity to desired products by the process of the instant invention. The result of Example 9 demonstrates that the use of several peroxygen additions during the reaction period can increase the substrate conversion. The result of Example 10 demonstrates that the use of several peroxygen additions and several source of bromide additions during the reaction period can significantly increase substrate conversion, and also increase the selectivity to aldehyde. The results of Examples 11, 12 and 13 clearly demonstrate the benefits that can be obtained by adding water to the reaction medium prior to the addition of the peroxygen compound, particularly in Example 13 where a high selectivity to aldehyde was achieved, with no monobrominated product being detected.

We claim:

1. A catalysed process for the oxidation of alkylaromatic compounds with a peroxygen compound in an aqueous reaction medium, wherein the catalyst comprises a source of cerium (III) or (IV), the reaction medium comprises a source of bromide ions and a solvent selected from the group consisting of carboxylic acids and anhydrides, and the alkylaromatic compound comprises an alkyl hydrogen atom bonded to the carbon alpha to the aromatic ring, whereby said process is effective at producing aldehyde or lower oxidized intermediate oxidation products in preference to carboxylic acid.

2. A process according to claim 1, wherein the alkyl substituent of the alkylaromatic compound comprises from 1 to 6 carbon atoms.

3. A process for the selective oxidation of methylaromatic compounds to aldehydes with a peroxygen compound in an aqueous reaction medium, characterised in that the catalyst comprises a source of cerium (III) or (IV), and the reaction medium comprises a source of bromide ions and a solvent selected from the group consisting of carboxylic acids and anhydrides.

4. A process according to claim 1 or claim 3, wherein the source of cerium is in the oxidation state cerium (III).

5. A process according to claim 4, wherein the source of cerium is selected from the group consisting of cerium metal, oxides, hydroxides, halides, carbonates, sulphates, acetates and nitrates.

6. A process according to claim 1 or claim 3, wherein the source of cerium comprises cerium (III) acetate.

7. A process according to claim 1 or claim 3, wherein the source of bromide ions is selected from the group consisting of bromine, hydrogen bromide, sodium bromide, potassium bromide, magnesium bromide, calcium bromide, cerium bromide and ammonium bromide.

8. A process according to claim 7, wherein the source of bromide comprises sodium bromide.

9. A process according to claim 1 or claim 3, wherein the carboxylic acid or carboxylic anhydride solvent comprises from 1 to 6 carbon atoms.

10. A process according to claim 9, characterised in that the solvent comprises acetic acid or propionic acid.

11. A process according to claim 1 or claim 3, wherein the mole ratio of alkylaromatic:cerium source is less than about 5000:1.

12. A process according to claim 11, wherein the mole ratio of alkylaromatic:cerium source is from about 3000:1 to about 10:1.

13. A process according to claim 1 or claim 3, wherein the mole ratio of cerium source to bromide ion source is selected in the range from about 10:1 to about 1:3000.

14. A process according to claim 1 or claim 3, wherein the peroxygen compound is selected from the group consisting of hydrogen peroxide, urea peroxide, sodium percarbonate, sodium perborate and peracids.

15. A process according to claim 1 or claim 3, wherein the peroxygen compound comprises hydrogen peroxide.

16. A catalysed process according to claim 1, wherein the catalyst comprises cerium triacetate, the reaction medium comprises sodium bromide and acetic acid, and the alkylaromatic compound comprises a methyl group.

17. A process according to claim 1 or claim 3, wherein the peroxygen compound is introduced into a reaction medium which contains both the substrate and catalyst system, and wherein said reaction medium comprises a mixture of carboxylic acid and water prior to the commencement of the introduction of the peroxygen compound.

18. A process according to claim 17, wherein the amount of water in the reaction medium prior to the addition of the peroxygen compound is from 5 to 30% by weight, based on the weight of carboxylic acid.

19. A process according to claim 1 or claim 3, wherein the aromatic ring of the alkyl aromatic or methyl aromatic compound is additionally substituted by one or more alkyl or halo groups.

20. A process according to claim 1 or claim 3, wherein a plurality of additions of peroxygen compound at intervals during the reaction period are employed.

21. A process according to claim 20, wherein a plurality of additions of source of bromide ions at intervals during the reaction period are employed.

22. A process according to claim 12, wherein the mole ratio of alkylaromatic:cerium source is from about 2500:1 to about 1500:1.

23. A process according to claim 13, wherein the mole ratio of cerium source to bromide ions source is from about 1:100 to about 1:1500.

24. A process according to claim 1 or claim 3 wherein the aromatic ring of the alkyl aromatic or methyl aromatic compound is additionally substituted by an alkyl group.

* * * * *